United States Patent
Gumm et al.

[19]
[11] Patent Number: 6,080,318
[45] Date of Patent: Jun. 27, 2000

[54] HPLC-BASED DEVICE AND METHOD FOR SEPARATING HIGH COMPLEX SUBSTANCE MIXTURES

[75] Inventors: Holger Gumm; Lutz Müller-Kuhrt, both of Berlin, Germany

[73] Assignee: Analyticon AG Biotechnologie Pharmazie, Germany

[21] Appl. No.: 09/269,372

[22] PCT Filed: Sep. 17, 1997

[86] PCT No.: PCT/EP97/05093

§ 371 Date: Apr. 8, 1999

§ 102(e) Date: Apr. 8, 1999

[87] PCT Pub. No.: WO98/13118

PCT Pub. Date: Apr. 2, 1998

[30] Foreign Application Priority Data

Sep. 25, 1996 [DE] Germany ............................ 196 41 210
Sep. 25, 1996 [DE] Germany ....................... 296 17 376 U

[51] Int. Cl.[7] ................................................. B01D 15/08
[52] U.S. Cl. ....................... 210/659; 210/656; 210/198.2
[58] Field of Search .................................... 210/635, 656, 210/659, 198.2; 422/70; 436/161

[56] References Cited

U.S. PATENT DOCUMENTS

| | | | |
|---|---|---|---|
| 4,454,043 | 6/1984 | Ting | 210/659 |
| 4,724,081 | 2/1988 | Kawahara | 210/659 |
| 4,806,250 | 2/1989 | Takata | 210/659 |
| 5,443,734 | 8/1995 | Fetwer | 210/656 |
| 5,503,805 | 4/1996 | Sugarman | 422/131 |
| 5,641,406 | 6/1997 | Sarhaddar | 210/198.2 |
| 5,705,061 | 1/1998 | Moran | 210/198.2 |
| 5,792,431 | 8/1998 | Moore | 422/134 |
| 5,872,010 | 2/1999 | Karger | 210/198.2 |
| 5,906,724 | 5/1999 | Sammons | 210/198.2 |

FOREIGN PATENT DOCUMENTS 32 24 495  12/1983  Germany ............................ 210/659

*Primary Examiner*—Ernest G. Therkorn
*Attorney, Agent, or Firm*—Londa & Gluck LLP

[57] ABSTRACT

The invention concerns an HPLC-based device and method for separating high complex substance mixtures. Plant and microbial extracts are high complex substance mixtures. They contain large amounts of extremely polar and non-polar materials. In principle, said mixtures can be separated by using a chromatic method. However, separation with existing chromatographic devices, for instance HPLC installations, is extremely time-consuming. The invention seeks to create a HPLC installation that separates fully automatically high complex substances in a very short time in such a way that said substances are broken down into their components in an almost pure state and can then be fed into a test system. To this end, said HPLC-based device comprises separation column units (A, F), fractionating column units (E, G), detector units (7, and 20, 21), pumping units (B, C, D) and fraction collecting units. These units, including all separating or fractionating columns, are interconnected and controlled by multiple way valves and by a computer unit that ensures the software-controlled operational interaction of the device.

29 Claims, 1 Drawing Sheet

HPLC-BASED DEVICE AND METHOD FOR SEPARATING HIGH COMPLEX SUBSTANCE MIXTURES

REFERENCE TO RELATED APPLICATIONS

This application is a 371 of PCT/EP97/05093 filed Sep. 17, 1997.

The invention relates to an HPLC-based apparatus and method for separating highly complex mixtures of substances.

BACKGROUND OF THE INVENTION

More than one third of the medicinal drugs currently on the market contain active ingredients, which nature has made available, that is, they were isolated from plants or microorganisms or, at the very least, modified on this basis.

In spite of this relatively large number of biological active substance, which nature has made available, worldwide efforts have, until now, been concentrated more on the chemical synthesis than on the so-called pool of natural products. In recent years, however, new active ingredients were discovered, which were created by nature and, as a result, natural products chemistry or natural products biochtechnology has therefore experienced a renaissance.

At the same time, with the discovery or production of new active ingredients, there was a rapid development in the sector of test system capacities. Whereas such biological assays for finding potentially new active ingredients some years ago required a few 100 mg of substance and, with that, only a few throughputs of tests per year were possible, the situation at the present time is basically different. As a result of test designs, which assume, for example, the inhibition of a specific enzyme as a measure of the biological activity, miniaturized automatic test machine can be realized, with which a million substances per year can be investigated, while at the same time little substance is consumed. The presence of these enormous test system capacities meets the requirements of natural products research, because frequently, until it is possible to detect a special biological activity, only a few milligrams of pure natural products, isolated from plants or microbial fermentations, are available.

Although a large number of natural products is already known, it must be assumed that nature has on hand a much larger number of substances, which until now have not been known, so that a high throughput screening of a large number of crude plant and microbial extracts cannot be avoided.

However, the testing of natural products requires a protracted procedure of preliminary purification, preliminary separation, intermediate purification and final purification, which must always be interrupted once again by testing for biological activity. This procedure requires much time, a large effort by personnel and a large logistic expenditure and moreover frequently leads to chemical substances, which are not worthwhile following up further.

In view of the cost pressures, which are carried over from the Public Health Service into the researching facilities, such time losses lead to constantly greater disadvantages for research and development, based on natural products research. Plant and microbial extracts are highly complex mixtures of substances. They contain extremely polar as well as nonpolar materials in large numbers. Basically, the separation of these mixture is possible with chromatographic methods. However, the time required for the separation with previously known chromatographic equipment, such as HPLC equipment, is unjustifiably high.

In the BEO 1994 annual report of the Bundesministerium für Bildung, Wissenschaft, Forschung und Technology (Federal Ministry for Education, Science, Research and Technology) pages 413 and 414, HPLC equipment for the isolation of natural products is described, which is intended to fractionate plant and microbial extracts coarsely and finely.

The equipment has the following disadvantages:

The fraction-collecting columns, named were, are connected over 12-way valves, the use of which for preparative applications is very expensive. The frequency of the switching required here leads to more rapid wear of components and seals.

A variable use, corresponding to the mixture that is to be separated, by increasing or decreasing the number of columns, is not possible, that is, because of this design, a modular construction of the equipment is not possible.

The large number of fraction-collecting columns leads to a long running time and to a high consumption of solvents.

An inexpensive and time-saving roll-over operation is not possible.

The isocratic separation in the second separation step, which is provided for here, also leads to a disadvantageous extension of the running time.

SUMMARY OF THE INVENTION

It is now an object of the invention to offer HPLC equipment, which separates highly complex mixtures of substances fully automatically in a very short time to such an extent, that the components are present in an almost pure form and can then be supplied to the test system.

This objective is accomplished with an apparatus and a method, which are based on HPLC and defined in claims 1 and 22.

The technology of separating the extracts, which forms the basis of the invention, is high-pressure liquid chromatography, which is in a position to separate relatively polar as well as nonpolar compounds. Because of the large number of substances in a complex mixture of substances, such as in plant and microbial extracts, the separation cannot be carried out in one step. Rather, the inventive combination of several systems of separating columns is necessary, in order to achieve a separation in a justifiable time.

The invention has various advantages. For example, the invention enables coarse and fine separation to be carried out in one piece of equipment and separated fractions to be stored on an interim basis on solid phases from which they can be recovered at any time, so that practically a complete separation of all substance fractions can be achieved within a very short time by means of software-controlled equipment. By these means, it is conceivable that, if the infrastructure is suitable, that is, if appropriate test systems, associated with a structure clarification system, are present, an identification of the effective components of an extract within 2 to 3 days becomes possible. This means an extreme acceleration of the process of finding active ingredients, a process which, starting out from mixtures of natural products such as plant or microbial extracts, usually takes months. Advantageously, the inventive apparatus has a modular construction, which enables expansions to be made, depending on the complexity of the mixtures of substances, which are to be separated.

BRIEF DESCRIPTION OF THE DRAWING

The invention is described in greater detail by means of a drawing, in which.

DESCRIPTION OF THE PREFERRED EMBODIMENTS

Figure 1:
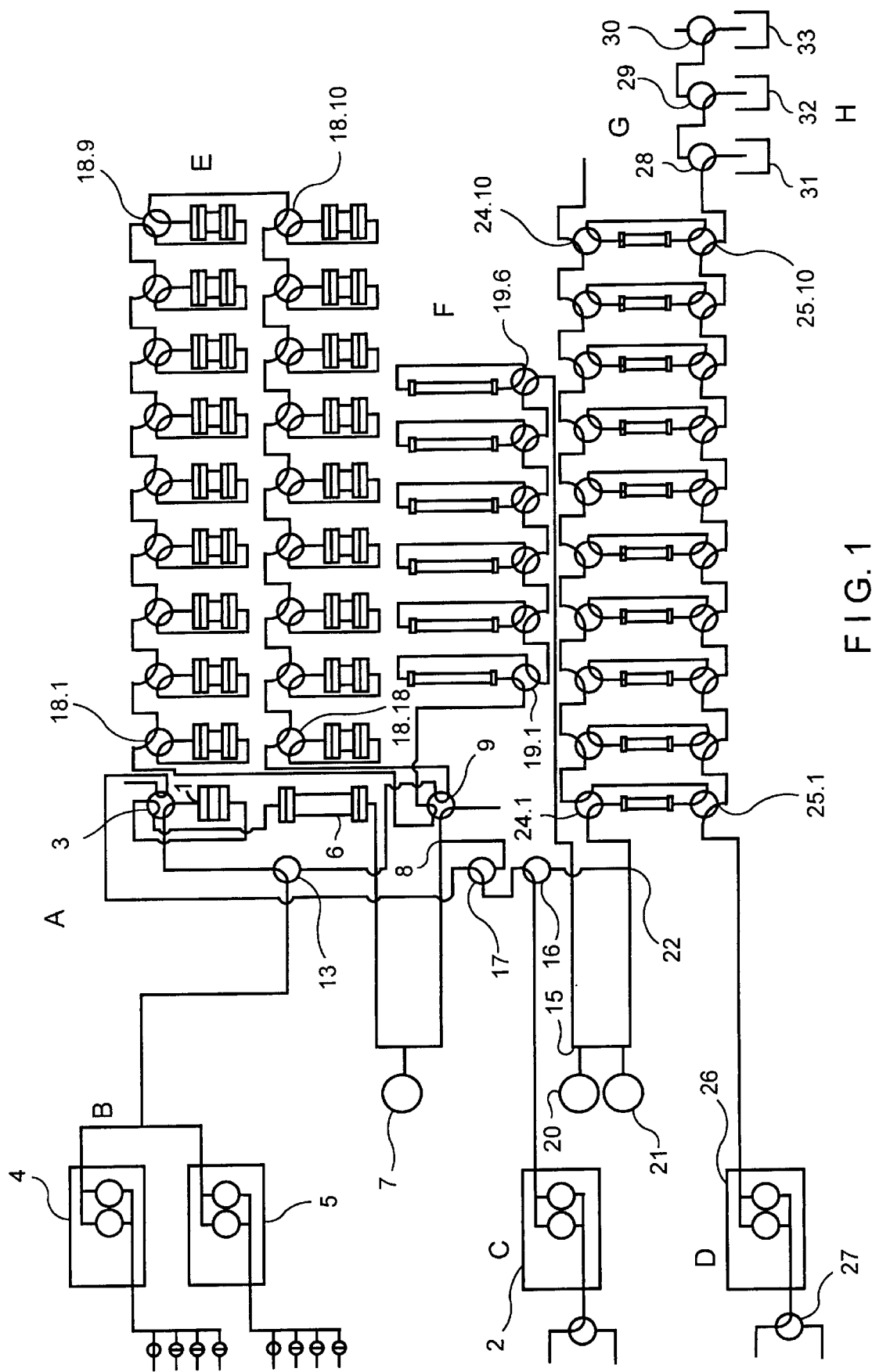
FIG. 1 shows the construction and flow diagram of the apparatus.

The multi-component mixture, which is to be separated (such as a plant or microbial extract, etc.) is dissolved in methanol and mixed with RP-4 material (particle size about 40 μm) in the ratio by weight of 1 part of extract to 3 parts of RP-4 material. The solvent is removed from this mixture in a rotary evaporator, so that a flowable mixture of extract and RP-4 material is formed. The mixture is filled dry into feeding column 1, which is installed in unit A, which holds the separating columns.

The air is removed from the feeding column 1, which was filled dry, with the help of a pump 2 and water as eluant over the 3-way valves 16, 17 and over a 6-way valve 3. When the air has been removed, the separating program, which is controlled by software, is started.

A gradient from 0% to 100% of the solvent or of the elements, conveyed with pump 5, is run 60 minutes with a pump 4 and a pump 5 of the pump unit B. Pump 4 pumps an aqueous buffer solution and pump 5 pumps a methanol solution. The components of the extract are flushed as a function of their polarity from the feeding column 1 over the 6-way valve 3 onto the separating column 6. The separating column 6 is filled with RP-4 material. The components are detected in a UV detector 7 and recorded with the software. The components reach a T piece 8 where water is metered into the eluant over pump 2 and the 3-way valves 16, 17 and the polarity of the solution is increased by these means. After that, this eluate passes through a 6-way valve 9 and reaches a fractionating columns unit E, which consists of 18 fractionating columns.

The fractionating columns of the fractionating columns unit E are filled with different adsorbents, at which the components are extracted by solid phase extraction.

Each fractionating column is connected for a period of 3 to 4 minutes. The fractionating columns are connected into the eluant stream over respective 4-way valves 18.1 to 18.18. By these means, the 60-minute gradient is divided into 18 fractions. The component-free eluate reaches the waste through the 6-way valve 9.

Each of the individual fractions, stored on the 18 fractionating columns, is separated further over one of the 6 separating columns of a separating columns unit F. At the same time, the components are back flushed from one of the fractionating columns by pump 4 and pump 5 of the pump unit B, over the 3-way valve 13, the 6-way valve 9 and over the corresponding 4-way valve 18.1 to 18.18 onto one of the 6 separating columns of the separating columns unit F and the components are separated further. The 6 separating columns are connected over appropriate 4-way valves 19.1 to 19.6.

After the separating column F, the separated components reach a splitter valve 15, which supplies a portion of the volume flowing (approximately ¹⁄₄₀) to a light-scattering detector 20. The remaining volume flowing passes through a UV detector and reaches a T piece 22, where water is added by the pump 2, and through a 3-way valve 16 to the eluate and the polarity of the solution is increased by these means. This eluate then reaches a fractionating column unit G, which is connected over ten 4-way valves 14.1 to 14.10 and coated with the separated components, the components being extracted from the eluate by the column material. These valves are controlled by a combination of identifying peaks by the detectors 20, 21 and by time control.

The valves are controlled by the control program in such a manner, that, when the first fractionating column is charged, methanol is pumped with the help of a pump 26 of a pumping unit D over a 3-way valve 27 through the corresponding 4-way valve 25.1 onto the first fractionating column and the components are flushed through the 3-way valves 28, 29, 30 into one of the fraction collectors 31, 32, 33 of the fraction collecting unit H. The fractionating column, rinsed clean, is conditioned with water over the 3-way valve 27 by means of the pump 26 and over the appropriate 4-way valve 28.1 for the next fractionation.

By these means, more than 10 fractions can be processed, because the fractionation is carried out simultaneously on the fractionating columns and the fractionating columns are also flushed and conditioned and thus prepared for a further fractionation.

---

List of Reference Symbols 1. feeding column
2. pump
3. 6-way valve
4. pump (B)
5. pump (B)
6. separating column
7. UV detector
8. T piece
9. 6-way valve
13. 3-way valve
15. splitter valve
16. 3-way valve
17. 3-way valve
18. 4-way valve (18.1–18.18)
19. 4-way valve (19.1–9.6)
20. light scattering detector
21. UV detector
22. T piece
24. 4-way valve (24.1–24.10)
25. 4-way valve (25.1–25.10)
26. pump (D)
27. 3-way valve
28. 3-way valve
29. 3-way valve
30. 3-way valve
31. fraction collector
32. fraction collector
33. fraction collector
A) separating column unit
B) pump unit
C) pump unit
D) pump unit
E) fractionating columns unit
F) separating columns unit
G) fractionating columns unit
H) fractionating columns unit

---

What is claimed is:

1. An apparatus, based on HPLC, for separating highly complex mixtures of substances, comprising
   separating columns units (A, F)
   fractionating columns units (E, G)
   detector units (7, 20, 21)
   pump units (B, C)
   fraction collector units (H) and
   a computer unit for the software-controlled functional collaboration of the apparatus, wherein the fractionating columns of the fractionating columns unit (E) and the separating columns of the separating columns unit (F) each have a 4-way valve (18.1–18.18 and 19.1–19.6), that the fractionating columns of the fractionating columns unit (G) each have two 4-way valves (24.1–24.10 and 25.1–25.10) and the 4-way valves (24.1–24.10, 25.1–25.10) of the fractionating columns unit (G) are connected selectably with a further pumping unit (D), wherein the separating column units (A, F) and fractionating column units (E, G) are disposed alternately.

2. The apparatus of claim 1, wherein it has at least two separating column units (A, F).

3. The apparatus of claim 1, wherein it has at least two fractionation units (E, G).

4. The apparatus of claim 1, wherein it has at least one detector unit (20, 21).

5. The apparatus of claim 1, wherein it has at least three pump units (B, C, D).

6. The apparatus of claim 1, wherein a separating columns unit (A) contains a feeding column and a separating column, connected in series, and the further separating column units (F) comprise at least two separating columns.

7. The apparatus of claim 1, wherein the separating columns unit (A) consists of a feeding loop and a separating column.

8. The apparatus of claim 1, wherein at least two detector units (7, 20, 21) are contained, which are disposed between separating column units (A, F) and fractionating units (E, G).

9. The apparatus of claim 1, wherein it has at least one detector unit (20, 21) comprising a detector that is selective and a detector that is not selective.

10. The apparatus of claim 1, wherein the detectors are UV and light-scattering detectors.

11. The apparatus of claim 1, wherein it has a mass-selective detector, such as a mass spectrometer.

12. The apparatus of claim 1, wherein at least three pumping units (B, C, D) are contained, at least one pumping unit (B) having at least two high pressure gradient pumps (4–5).

13. The apparatus of claim 1, wherein the pumping units (B, C, D) are connected over multi-way valves with the fractionating column units (E, G) and the separating columns units (A, F).

14. The apparatus of claim 1, wherein the separating columns of the separating column units (A, F) are filled with reverse phase materials (RP).

15. The apparatus of claim 1, wherein the separating columns of the separating columns unit (A, F) and the fractionating columns of the fractionating columns unit (E, G) are filled with normal and reverse phase materials.

16. The apparatus of claim 1, wherein the separating columns and fractionating columns are filled with silica gel, with modified silica gels and/or with polymer phases.

17. The apparatus of claim 1, wherein the pumping unit (B), the separating columns unit (A) and the fractionating columns unit (E) are selectably connected with one another over a 6-way valve (3).

18. The apparatus of claim 1, wherein the fractionating columns unit (E) and the separating columns unit (F) are connected controllably with one another over a 6-way valve (9).

19. An HPLC-based method for separating highly complex mixtures of substances, comprising the following steps:

gradient separation of a highly complex mixture of substances in a first separating columns unit (A) into a defined number of fractions by means of a pump unit (B)

increasing the polarity of the eluant by the addition of water by means of a pumping unit (C)

transferring the fractions to a first fractionating columns unit (G), the number of columns of which corresponds to the number of separated fractions, and absorbing the previously separating fractions on a fractionating column each by solid phase extraction sequentially flushing the fractions, absorbed in the first fractionating columns unit (E), with less polar eluants into a second separating columns unit (F)

increasing the polarity of the eluant by adding water over a pumping unit (C)

sequentially transferring the fractions, which have been separated further, in accordance with the signals of the detector unit (20, 21) into a fractionating columns unit (G) and absorbing each fraction on a fractionating column by solid phase extraction, wherein there is a further fractionation of the second separating columns unit (F) with the weak gradient by means of the pump unit (B), that there is a sequential flushing of the fractions from the fractionating columns unit (G) into the fraction collector unit (H) by means of a pump unit (D) and a less polar eluant and a subsequent conditioning of the fractionating column, flushed clean, by means of the pump unit (D), and that there is transport of the mobile phase and there are conditioning steps or equilibrating steps of the individual columns in the separating columns unit, which are required in the interim, by controlling the pump units (B, C, D), by switching the multi-way valves and controlling the fraction collector while processing the signals of the detector units (7 and 20, 21) using a computer unit.

20. The method of claim 19, wherein the addition of the mobile phase to each individual separating column of the separating columns unit (F) and each individual fractionating column of the fractionating columns unit (E, G) is carried out separately, under the control of a computer, over 4-way valves.

21. The method of claim 19, wherein, after a fractionating column of the fractionating columns unit (G) in a fraction collector (31, 32, 33) of the fraction collector unit (H) is flushed to clean it by means of the pump unit (D), the fractionating column is conditioned for the next fractionation.

22. The method of claim 19, wherein the highly complex mixture of substances is supplied to the apparatus over a supplying column.

23. The method of claim 19, wherein the highly complex mixture of substances is mixed with an adsorbent and suspended in a solvent such as methanol, after which the solvent is removed and the adsorbent, charged with the complex mixture of substances, is filled into the supplying column.

24. The method of claim 19, wherein the separation of the mixture of substances in the separating columns unit (A) is accomplished with a gradient of increasing lipophilicity.

25. The method of claim 19, wherein aqueous buffer solutions and lipophilic solvents are used as eluants.

26. The method of claim 19, wherein solvents from the group consisting of, are used as lipophilic solvents.

27. The method of claim 19, wherein a peak identification program is used, which permits the number of fractions to be optimized.

28. The method of claim 19, wherein different adsorbents, corresponding to the polarity of the fraction, are used in the columns of the fractionating columns unit (E, G).

29. The method of claim 19, wherein the fractionating columns are cleaned by back flushing.

* * * * *